US008828946B2

(12) United States Patent
Wehling et al.

(10) Patent No.: US 8,828,946 B2
(45) Date of Patent: Sep. 9, 2014

(54) COMPOSITION COMPRISING INTERLEUKIN-1 RECEPTOR ANTAGONIST AND CORTICOSTEROID

(75) Inventors: Peter Wehling, Dusseldorf (DE); Julio Reinecke, Cologne (DE)

(73) Assignee: Orthogen AG, Düsseldorf (DE)

( * ) Notice: Subject to any disclaimer, the term of this patent is extended or adjusted under 35 U.S.C. 154(b) by 0 days.

(21) Appl. No.: 13/142,577

(22) PCT Filed: Dec. 10, 2010

(86) PCT No.: PCT/EP2010/069427
§ 371 (c)(1),
(2), (4) Date: Nov. 7, 2011

(87) PCT Pub. No.: WO2011/082951
PCT Pub. Date: Jul. 14, 2011

(65) Prior Publication Data
US 2012/0237525 A1    Sep. 20, 2012
US 2013/0164303 A2    Jun. 27, 2013

(30) Foreign Application Priority Data
Dec. 10, 2009    (DE) .......................... 10 2009 057 495

(51) Int. Cl.
*A61K 38/20* (2006.01)
*A61K 31/573* (2006.01)
*A61K 45/06* (2006.01)
*A61K 35/14* (2006.01)
*A61K 9/00* (2006.01)
*A61K 9/51* (2006.01)
*A61K 38/00* (2006.01)

(52) U.S. Cl.
CPC ............. *A61K 38/20* (2013.01); *A61K 2300/00* (2013.01); *A61K 9/0014* (2013.01); *A61K 9/0019* (2013.01); *A61K 9/5184* (2013.01); *A61K 31/573* (2013.01); *A61K 45/06* (2013.01); *A61K 38/00* (2013.01); *A61K 35/15* (2013.01); *A61K 35/19* (2013.01)
USPC ............. 514/21.2; 514/7.6; 514/8.1; 514/8.5; 514/8.8; 514/8.9; 514/9.5

(58) Field of Classification Search
CPC . A61K 2300/00; A61K 31/573; A61K 38/00; A61K 38/20
USPC ............... 514/21.2, 7.6, 8.1, 8.5, 8.8, 8.9, 9.5
See application file for complete search history.

(56) References Cited

U.S. PATENT DOCUMENTS

| 5,994,094 A | 11/1999 | Hötten |
| 6,623,472 B1 | 9/2003 | Reincke |
| 2008/0286379 A1 | 11/2008 | Wehling et al. |
| 2009/0047242 A1 | 2/2009 | Reinecke et al. |

FOREIGN PATENT DOCUMENTS

| EP | 0 343 684 A1 | 5/1989 |
| EP | 0 904 112 B1 | 11/2009 |
| WO | WO95/04819 | 2/1995 |
| WO | WO 00/46249 | 8/2000 |
| WO | WO 03/080122 A1 | 10/2003 |
| WO | WO 2006/007529 A2 | 1/2006 |

OTHER PUBLICATIONS

Fleischmann, Roy et al.: "Anakinra, a Recombinant Human Interleukin-1 Receptor Antagonist (r-metHuIL-1ra), in Patients With Rheumathoid Arthritis", in Arthritis & Rheumatism, vol. 48, No. 4, Apr. 2003, p. 927-934.
Brenner, M et al.: "Targeted treatment of pyoderma gangrenosum in PAPA (pyogenic arthritis, pyoderma gangrenosum and acne) syndrome with the recombinant human interleukin-1 receptor antagonist anakinra", in: Br J Dermatol, Nov. 2009, 161 (5): 1199-201, Abstract.
Neustadt, David H., "Intra-articular injections for osteoarthritis of the knee" Cleveland Clinic Journal of Medicine, (2006) vol. 73 No. pp. 897-911.
Evans, CH, "Novel Biological Approaches in the Intra-Articular Treatment of Osteoarthiritis", Biodrugs, (2005) vol. 19 (6), pp. 355-362.
Barry Bresnihan, et. al.:"Treatment of Rheumatoid Arthritis with . . . " in: Arthritis & Rheumatism, Dec. 12, 1998.
Lucas D. Settas, et. al.: "Reactivation of Pulmonary Tuberculosis . . . ", in: Journal of Clinical Rheumatology, Aug. 4, 2007.
Nicole R. Bianco et. al.: "Therapeutic Effect of Exosomes from Indoleamine . . . " in:Arthritis & Rheumatism, Feb. 2009.
F. U. Hornstein: "Orthokotin . . . ", in: Arznei-Telegramm, No. 3 2001.
Auw Yang et al.: "Autologous interleukin-1 receptor antagonist improves function and szmptoms in osteorarthritis . . . ", in: Osteoarthritis Cartillage, Apr. 2008, vol. 16, Iss. 4, pp. 498-505.
"108. Ostheoarthritis", in: "The Merck Manual" Moscow, Mir 1997, p. 910, left column, § 1-2, 4.
"Arthrosis", in: Encyclopedic Dictionary of Medical Terms, M, Medicine, Moscow 2001, p. 64.

*Primary Examiner* — Prema Mertz
(74) *Attorney, Agent, or Firm* — Henry M. Feiereisen LLC; Ursula B. Day

(57) ABSTRACT

The present invention relates to pharmaceutical compositions for a combination therapy with a cytokine antagonist and a corticosteroid. By means of the combination therapy diseases such as osteoarthritis, tendon injuries and/or degenerative spinal diseases can be treated.

21 Claims, No Drawings

SEQUENCE LISTING

<160> NUMBER OF SEQ ID NOS: 8

<210> SEQ ID NO 1
<211> LENGTH: 177
<212> TYPE: PRT
<213> ORGANISM: Homo sapiens

<400> SEQUENCE: 1

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 2
<211> LENGTH: 159
<212> TYPE: PRT
<213> ORGANISM: Homo sapiens

<400> SEQUENCE: 2

```
Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
```

```
                65                  70                  75                  80
Asp Glu Thr Arg Leu Gln Leu Glu Ala Val Asn Ile Thr Asp Leu Ser
                    85                  90                  95

Glu Asn Arg Lys Gln Asp Lys Arg Phe Ala Phe Ile Arg Ser Asp Ser
                    100                 105                 110

Gly Pro Thr Thr Ser Phe Glu Ser Ala Ala Cys Pro Gly Trp Phe Leu
                    115                 120                 125

Cys Thr Ala Met Glu Ala Asp Gln Pro Val Ser Leu Thr Asn Met Pro
130                 135                 140

Asp Glu Gly Val Met Val Thr Lys Phe Tyr Phe Gln Glu Asp Glu
145                 150                 155

<210> SEQ ID NO 3
<211> LENGTH: 180
<212> TYPE: PRT
<213> ORGANISM: Homo sapiens

<400> SEQUENCE: 3

Met Ala Leu Ala Asp Leu Tyr Glu Glu Gly Gly Gly Gly Gly Gly Glu
1               5                   10                  15

Gly Glu Asp Asn Ala Asp Ser Lys Glu Thr Ile Cys Arg Pro Ser Gly
                20                  25                  30

Arg Lys Ser Ser Lys Met Gln Ala Phe Arg Ile Trp Asp Val Asn Gln
                35                  40                  45

Lys Thr Phe Tyr Leu Arg Asn Asn Gln Leu Val Ala Gly Tyr Leu Gln
            50                  55                  60

Gly Pro Asn Val Asn Leu Glu Glu Lys Ile Asp Val Val Pro Ile Glu
65                  70                  75                  80

Pro His Ala Leu Phe Leu Gly Ile His Gly Gly Lys Met Cys Leu Ser
                    85                  90                  95

Cys Val Lys Ser Gly Asp Glu Thr Arg Leu Gln Leu Glu Ala Val Asn
                    100                 105                 110

Ile Thr Asp Leu Ser Glu Asn Arg Lys Gln Asp Lys Arg Phe Ala Phe
                115                 120                 125

Ile Arg Ser Asp Ser Gly Pro Thr Thr Ser Phe Glu Ser Ala Ala Cys
            130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                    165                 170                 175

Gln Glu Asp Glu
            180

<210> SEQ ID NO 4
<211> LENGTH: 143
<212> TYPE: PRT
<213> ORGANISM: Homo sapiens

<400> SEQUENCE: 4

Met Gln Ala Phe Arg Ile Trp Asp Val Asn Gln Lys Thr Phe Tyr Leu
1               5                   10                  15

Arg Asn Asn Gln Leu Val Ala Gly Tyr Leu Gln Gly Pro Asn Val Asn
                20                  25                  30

Leu Glu Glu Lys Ile Asp Val Val Pro Ile Glu Pro His Ala Leu Phe
                35                  40                  45

Leu Gly Ile His Gly Gly Lys Met Cys Leu Ser Cys Val Lys Ser Gly
```

```
                50                  55                  60
Asp Glu Thr Arg Leu Gln Leu Glu Ala Val Asn Ile Thr Asp Leu Ser
 65                  70                  75                  80

Glu Asn Arg Lys Gln Asp Lys Arg Phe Ala Phe Ile Arg Ser Asp Ser
                 85                  90                  95

Gly Pro Thr Thr Ser Phe Glu Ser Ala Ala Cys Pro Gly Trp Phe Leu
            100                 105                 110

Cys Thr Ala Met Glu Ala Asp Gln Pro Val Ser Leu Thr Asn Met Pro
        115                 120                 125

Asp Glu Gly Val Met Val Thr Lys Phe Tyr Phe Gln Glu Asp Glu
    130                 135                 140

<210> SEQ ID NO 5
<211> LENGTH: 155
<212> TYPE: PRT
<213> ORGANISM: Homo sapiens

<400> SEQUENCE: 5

Met Val Leu Ser Gly Ala Leu Cys Phe Arg Met Lys Asp Ser Ala Leu
  1               5                  10                  15

Lys Val Leu Tyr Leu His Asn Asn Gln Leu Leu Ala Gly Gly Leu His
                 20                  25                  30

Ala Gly Lys Val Ile Lys Gly Glu Glu Ile Ser Val Val Pro Asn Arg
             35                  40                  45

Trp Leu Asp Ala Ser Leu Ser Pro Val Ile Leu Gly Val Gln Gly Gly
         50                  55                  60

Ser Gln Cys Leu Ser Cys Gly Val Gly Gln Glu Pro Thr Leu Thr Leu
 65                  70                  75                  80

Glu Pro Val Asn Ile Met Glu Leu Tyr Leu Gly Ala Lys Glu Ser Lys
                 85                  90                  95

Ser Phe Thr Phe Tyr Arg Arg Asp Met Gly Leu Thr Ser Ser Phe Glu
            100                 105                 110

Ser Ala Ala Tyr Pro Gly Trp Phe Leu Cys Thr Val Pro Glu Ala Asp
        115                 120                 125

Gln Pro Val Arg Leu Thr Gln Leu Pro Glu Asn Gly Gly Trp Asn Ala
    130                 135                 140

Pro Ile Thr Asp Phe Tyr Phe Gln Gln Cys Asp
145                 150                 155

<210> SEQ ID NO 6
<211> LENGTH: 177
<212> TYPE: PRT
<213> ORGANISM: Equus caballus

<400> SEQUENCE: 6

Met Glu Ile Arg Arg Arg Ser Val Arg His Leu Ile Ser Leu Leu Leu
  1               5                  10                  15

Phe Leu Phe Tyr Ser Gly Thr Ala Cys His Pro Leu Gly Lys Arg Pro
                 20                  25                  30

Cys Lys Met Gln Ala Phe Arg Ile Trp Asp Val Asn Gln Lys Thr Phe
             35                  40                  45

Tyr Met Arg Asn Asn Gln Leu Val Ala Gly Tyr Leu Gln Glu Ser Asn
         50                  55                  60

Thr Lys Leu Gln Glu Lys Ile Asp Val Val Pro Ile Glu Pro Asp Ala
 65                  70                  75                  80

Leu Phe Leu Gly Leu His Gly Arg Lys Leu Cys Leu Ala Cys Val Lys
```

```
                85                  90                  95

Ser Gly Asp Glu Ile Arg Phe Gln Leu Glu Ala Val Asn Ile Thr Asp
            100                 105                 110

Leu Ser Lys Asn Lys Glu Glu Asn Lys Arg Phe Thr Phe Ile Arg Ser
        115                 120                 125

Asn Ser Gly Pro Thr Thr Ser Phe Glu Ser Ala Ala Cys Pro Gly Trp
    130                 135                 140

Phe Leu Cys Thr Ala Gln Glu Ala Asp Arg Pro Val Ser Leu Thr Asn
145                 150                 155                 160

Lys Pro Lys Glu Ser Phe Met Val Thr Lys Phe Tyr Leu Gln Glu Asp
                165                 170                 175

Gln

<210> SEQ ID NO 7
<211> LENGTH: 177
<212> TYPE: PRT
<213> ORGANISM: Equus caballus

<400> SEQUENCE: 7

Met Glu Ile Arg Arg Arg Ser Val Arg His Leu Ile Ser Leu Leu Leu
1               5                   10                  15

Phe Leu Leu Tyr Ser Glu Thr Ala Cys His Pro Leu Gly Lys Arg Pro
            20                  25                  30

Cys Lys Met Gln Ala Phe Arg Ile Trp Asp Val Asn Gln Lys Thr Phe
        35                  40                  45

Tyr Met Arg Asn Asn Gln Leu Val Ala Gly Tyr Leu Gln Glu Ser Asn
    50                  55                  60

Thr Lys Leu Gln Glu Lys Ile Asp Val Val Pro Ile Glu Pro Asp Ala
65                  70                  75                  80

Leu Phe Leu Gly Leu His Gly Arg Lys Leu Cys Leu Ala Cys Val Lys
                85                  90                  95

Ser Gly Asp Glu Ile Arg Phe Gln Leu Glu Ala Val Asn Ile Thr Asp
            100                 105                 110

Leu Ser Lys Asn Lys Glu Glu Asn Lys Arg Phe Thr Phe Ile Arg Ser
        115                 120                 125

Asn Ser Gly Pro Thr Thr Ser Phe Glu Ser Ala Ala Cys Pro Gly Trp
    130                 135                 140

Phe Leu Cys Thr Ala Gln Glu Ala Asp Arg Pro Val Ser Leu Thr Asn
145                 150                 155                 160

Lys Pro Lys Glu Ser Phe Met Val Thr Lys Phe Tyr Leu Gln Glu Asp
                165                 170                 175

Gln

<210> SEQ ID NO 8
<211> LENGTH: 176
<212> TYPE: PRT
<213> ORGANISM: Canis familiaris

<400> SEQUENCE: 8

Met Glu Thr Cys Arg Cys Pro Leu Ser Tyr Leu Ile Ser Phe Leu Leu
1               5                   10                  15

Phe Leu Ser His Ser Glu Thr Ala Cys Arg Pro Leu Gly Lys Arg Pro
            20                  25                  30

Cys Arg Met Gln Ala Phe Arg Ile Trp Asp Val Asn Gln Lys Thr Phe
        35                  40                  45
```

```
Tyr Leu Arg Asn Asn Gln Leu Val Ala Gly Tyr Leu Gln Gly Ser Asn
    50              55                  60
Thr Lys Leu Glu Glu Lys Leu Asp Val Val Pro Val Glu Pro His Ala
65              70                  75                      80
Val Phe Leu Gly Ile His Gly Gly Lys Leu Cys Leu Ala Cys Val Lys
                85                  90                  95
Ser Gly Asp Glu Thr Arg Leu Gln Leu Glu Ala Val Asn Ile Thr Asp
            100                 105                 110
Leu Ser Lys Asn Lys Asp Gln Asp Lys Arg Phe Thr Phe Ile Leu Ser
        115             120                 125
Asp Ser Gly Pro Thr Thr Ser Phe Glu Ser Ala Ala Cys Pro Gly Trp
    130             135                 140
Phe Leu Cys Thr Ala Leu Glu Ala Asp Arg Pro Val Ser Leu Thr Asn
145             150                 155             160
Arg Pro Glu Glu Ala Met Met Val Thr Lys Phe Tyr Phe Gln Lys Glu
                165             170                 175
```

COMPOSITION COMPRISING INTERLEUKIN-1 RECEPTOR ANTAGONIST AND CORTICOSTEROID

CROSS-REFERENCES TO RELATED APPLICATIONS

This application is the U.S. National Stage of International Application No. PCT/EP2010/069427, filed Dec. 10, 2010, which designated the United States and which claims the priority of German Patent Application, Serial No. 10 2009 057 495.6, filed Dec. 10, 2009, pursuant to 35 U.S.C. 119(a)-(d).

BACKGROUND OF THE INVENTION

1. Field of the Invention

The present invention relates to pharmaceutical compositions for a combination therapy with a cytokine antagonist and a corticosteroid. By means of the combination therapy diseases such as osteoarthritis (including inflammatory types of osteoarthritis), tendon conditions and/or degenerative spinal diseases can be treated, wherein the treatment is preferably carried out locally.

2. Technical Background

Osteoarthritis refers to "joint wear" to a higher degree than typical for a certain age. It is accompanied by a loss of cartilage in the respective joint, which results in pain and function deterioration. Excess strain, congenital or traumatic causes such as joint malpositions or also bone deformation through bone diseases like osteoporosis are viewed as causes. It can also result from another disease such as joint inflammation or accompany effusion caused by excess strain.

Generally all joints can be affected by osteoarthritic changes. In Germany the disease is most frequently located in the knee joint. Osteoarthritis is one of the most common reasons for seeking advice at a general practitioner's practice. Approximately 10% of the population in Western countries suffer from osteoarthritis. If osteoarthritis diseases of the small vertebral joints and the degenerative intervertebral disc diseases are added, even approx. 15%-20% of the population are affected. The risk of suffering from osteoarthritis increases with age. About two thirds of people over 65 years are affected by the disease, however, not all persons affected also suffer from the symptoms.

For the treatment of osteoarthritis some therapy forms are already known. This includes conservative (e.g. medicinal) therapies as well as surgical procedures to the point of replacing the complete joint by a prosthesis. In order to avoid these extensive and irreversible interventions, an effective medicinal treatment is generally preferred to delay the point in time of a complete joint replacement as far as possible.

However, many medicinal treatments also have disadvantages. On the one hand this is due to the side effects of the medicaments themselves, but their effects are also partially limited.

A medicinal agent frequently used for treating osteoarthritis is cortisone and related corticosteroids. These are administered systemically, however mostly locally as an injection into the affected joint. However, it is found that the positive effect of the corticosteroid already decreases after just one week. This is clinically proven by randomized studies and clinical experience.

A further medicament which can be used for treating osteoarthritis is the protein IL-1Ra, which is produced naturally in the body, or an isoform or fragment thereof, which shows a similar activity. Interleukin-1-receptor antagonist (IL-1Ra) binds to the same receptors on the cell surface as interleukin-1 (IL-1), but does not trigger the signalling cascade normally caused by IL-1Ra binding. By binding to the IL-1 receptor, IL-1Ra blocks the binding of IL-1 and thus prevents its transduction of signals and thus the inflammatory effect of IL-1 on the target cells.

Treatment of patients with autologous serum in which IL-1Ra was enriched and is contained therein among other factors, is known in the state of the art. IL-1Ra used in this way is also called Orthokine. A recombinant IL-1Ra fragment, Anakinra, in contrast surprisingly did not show any effects in the treatment of osteoarthritis compared to a placebo treatment. Anakinra is an isoform of the human interleukin-1 receptor antagonist shortened to amino acids 26-177 and terminally L-methionylated and has a sequence length of 153 amino acids. The preparation is done for example by means of *Escherichia coli* strains using recombinant methods.

In the light of the state of the art, the problem to be solved was thus to provide a medicinal treatment of osteoarthritis, which is more effective and particularly shows a good long-term efficacy.

SUMMARY OF THE INVENTION

Surprisingly it was now found that the efficacy, in particular the long-term efficacy of corticosteroids such as cortisone when treating osteoarthritis, inflammatory types of osteoarthritis and degenerative spinal diseases, can be significantly or synergistically improved by additional administration of a cytokine antagonist like Orthokine and Anakinra. This is particularly found when locally administering the therapeutics into the joint to be treated. In particular this is extremely surprising in the light of the fact that this advantageous effect occurs when additionally administering natural IL-1Ra such as Orthokine as well as recombinant IL-1Ra such as Anakinra, even though it is proven that Anakinra alone does not show any effect in the treatment of osteoarthritis and degenerative spinal diseases. The present invention creates the possibility of rendering the recombinant IL-1Ra suitable for a treatment of osteoarthritis and spinal diseases, as it is not suitable for the treatment of these diseases on its own. A similar, surprisingly good efficiency and high safety of the combination of these agents was also found for autoimmune diseases such as neurodermitis and alopecia areata, wherein mostly the anti-inflammatory effect plays a role.

A possible explanation for this fact is that the cytokine antagonists have an anabolic effect and can neutralize or even reverse the harmful catabolic effect of the corticosteroids in the affected joints. Thus, in the treatment of for example osteoarthritis, the corticosteroids can, apart from the cytokine antagonists, be alternatively or additionally combined with anabolic growth factors in order to achieve a similar or even potentiating effect. Thus the invention enables the preparation of a corticosteroid which does not have the known harmful effects in osteoarthritis, which can consist of increased cartilage destruction, by combining it with a cytokine antagonist.

Thus the present invention provides in a first aspect a pharmaceutical composition comprising a corticosteroid together with a cytokine antagonist and optionally a growth factor, wherein the cytokine antagonist is the naturally occurring or recombinant interleukin antagonist IL-1Ra protein, in particular Orthokine or Anakinra, and wherein the pharmaceutical composition is suitable for local administration.

The therapeutics may also be administered in two different pharmaceutical compositions simultaneously or sequentially.

Accordingly, the invention in a second and third aspect provides a pharmaceutical composition comprising a cytokine antagonist and optionally a growth factor for use in a combination therapy together with a corticosteroid as well as a pharmaceutical composition comprising a corticosteroid for use in a combination therapy together with a cytokine antagonist and optionally a growth factor. In the second as well as the third aspect of the invention, the cytokine antagonist is the naturally occurring or recombinant interleukin antagonist IL-1Ra protein, in particular Orthokine or Anakinra, and the pharmaceutical composition is suitable for local administration.

In a fourth aspect according to the invention a kit is provided comprising a pharmaceutical composition comprising a cytokine antagonist and optionally a growth factor and a pharmaceutical composition comprising a corticosteroid. The cytokine antagonist is the naturally occurring or recombinant interleukin antagonist IL-1Ra protein, in particular Orthokine or Anakinra, and the pharmaceutical compositions are suitable for local administration.

Furthermore, the invention in a fifth aspect relates to the use of a cytokine antagonist and optionally a growth factor for preparing a pharmaceutical composition for use in a combination therapy together with a corticosteroid and in a sixth aspect the use of a corticosteroid for preparing a pharmaceutical composition for use in a combination therapy together with a cytokine antagonist and optionally a growth factor. In the fifth as well as the sixth aspect of the invention the cytokine antagonist is the naturally occurring or recombinant interleukin antagonist IL-1Ra protein, in particular Orthokine or Anakinra, and the pharmaceutical composition is suitable for local administration.

Further embodiments of the invention are shown in the following detailed description and in the claims.

DESCRIPTION OF THE INVENTION

The invention is based on the surprising finding that the treatment of joint and spinal diseases such as osteoarthritis, arthritis, inflammatory types of osteoarthritis and degenerative spinal disease as well as autoimmune diseases by means of corticosteroids can be significantly improved by additional administration of a cytokine antagonist and optionally of a growth factor. In particular, in the case of treatment with the recombinant IL-1Ra, Anakinra, only by combination with a corticosteroid, an effect is achieved which is much higher than the sole effect of the corticosteroid or which makes Anakinra in combination with a corticosteroid an effective agent at all in the treatment of the mentioned diseases. In the case of the natural IL-1Ra Orthokine a significant improvement of efficacy is observable especially regarding inflammatory or inflammatory progressing osteoarthritis or inflammation of the vertebral joints or the nerve root. Thus the invention is directed towards the combination therapy of such diseases by means of a corticosteroid together with a cytokine antagonist like Anakinra or Orthokine and optionally of a growth factor.

These different agents may be administered simultaneously—in the same formulation or in different formulations—or sequentially. The pharmaceutical compositions according to the invention, that comprise only one of the two different agents, as well as the kit according to the invention, may be intended for simultaneous administration on the one hand and for sequential administration of the cytokine antagonist and the corticosteroid on the other hand. Simultaneous administration however is preferred, particularly in only one formulation. This way the two pharmaceutical compositions of the kit according to the invention, for example, may be mixed in an appropriate ratio before being administered to the patient and may then be administered as a formulation. When sequentially administering the cytokine antagonist and the corticosteroid, the different agents are preferably administered within a time period of one week, preferably within 5 days, 3 days, one day or within 12 hours.

According to the invention, the cytokine antagonist may be combined with a growth factor. Optionally, a further cytokine antagonist is contained in the pharmaceutical composition according to the invention or the kit according to the invention.

The cytokine antagonist used according to the invention may be any substance or any mixture of substances that reduces or inhibits at least one, preferably substantially all of the biological activities of one or more cytokines in the body of the patient. The antagonistic effect may occur directly by the antagonist or indirectly, e.g. by activating or inhibiting further signalling pathways that also have an effect on the biologic activity of the cytokine. Preferably the biological activity of the cytokine is inhibited by blocking its interaction with one or more receptors to which it can bind. This can be achieved for example by competitive binding of the antagonist to the corresponding receptor(s) or by binding of the antagonist to the cytokine itself. Preferably the cytokine antagonist inhibits the effect of the cytokine IL-1.

The cytokine may be e.g. a protein, a peptide, a nucleic acid, a lipid or an organic compound. The cytokine antagonist may also consist of a mixture of two or more cytokine antagonists as described herein. In particular the cytokine antagonist may be a naturally occurring peptide or protein or also a recombinantly prepared peptide or protein. Furthermore the cytokine antagonist may be or comprise an antibody or antigen-binding fragment of an antibody, particularly an antibody or antibody fragment which can bind the respective cytokine or a cytokine receptor. Examples for suitable cytokine antagonists are interleukin antagonists, particularly IL-1 antagonists like IL-1Ra, tumor necrosis factor (TNF) antagonists, particularly a TNF-α antagonist such as an anti-TNF-α antibody, interferon antagonists and chemokine antagonists. Particularly preferred is naturally occurring or recombinant IL-1Ra protein, preferably human IL-1Ra. IL-1Ra preferably comprises or preferably consists of the amino acid sequence of an isoform or a homologue of the human IL-1Ra according to SEQ ID NOs: 1, 2, 3, 4 or 5, an isoform of the equine IL-1Ra according to SEQ ID NOs: 6 or 7 or an isoform of the canine IL-1Ra according to SEQ ID NO:8. Preferably the pharmaceutical composition according to the invention or the kit according to the invention comprises such a cytokine antagonist in addition to the naturally occurring or recombinant IL-1Ra protein.

Furthermore, according to the invention, fragments or derivatives of IL-1Ra may be used as cytokine antagonist as long as they can exercise the desired function, i.e. the reduction or inhibition of one or more biological functions of IL-1. Fragments of IL-1Ra preferably comprise at least 20, more preferably at least 40, 60, 80 or at least 100 amino acids of a natural IL-1Ra sequence. Preferably the fragments are naturally occurring secreted fragments of IL-1Ra. In one embodiment, the IL-1Ra comprises amino acids 26 to 177 of the human IL-1Ra, preferably amino acids 26 to 177 of the sequence according to SEQ ID NO: 1. Derivates of IL-1Ra are preferably homologous to natural IL-1Ra and preferably have a homology or identity to natural IL-1Ra of at least 60%, more preferably at least 70%, 75%, 80%, 85%, 90%, 95% and most preferably at least 98% over an area of at least 20 contiguous amino acids, preferably at least 40, 60, 80 or at least 100 contiguous amino acids and most preferably over the total length of IL-1Ra. Particularly preferred is the IL-1Ra isolated from natural biological samples like blood, also called Orthokine, as well as the IL-1Ra fragment having amino acids 26 to 177 of human IL-1Ra, also called Anakinra. The preparation of Orthokine is described inter alia in Patent Application Nos. WO 00/46249 A1 and WO 03/080122 A1. Anakinra as well as further IL-1 antagonists that may be used in this invention are described inter alia in Patent Application EP 0 343 684 A1.

In the preparation of IL-1Ra from natural biological samples such as blood, like e.g. Orthokine, the obtained IL-1Ra solution preferably also contains growth factors, which may be responsible for the surprising efficacy of the combination of agents according to the invention. Thus, according to the invention, the cytokine antagonist may also be present in combination with one or more growth factors or be replaced by one or more growth factors according to the invention. The growth factor preferably has an anabolic effect. Examples for suitable growth factors are TGF-β, IGF, BMP, HGF and VEGF. Also comprised are analogues, derivatives and fragments of these growth factors as long as they have the desired effect, i.e. particularly their effect as growth factor.

The corticosteroid used according to the invention may be any naturally occurring as well as synthetically prepared corticosteroid. It may particularly be a glucocorticoid, a mineralcorticoid or an androgen, wherein glucocorticoids are preferably used. A mixture from two or more corticosteroids as described herein may also be used. Examples for glucocorticoids are cortisone, hydrocortisone, prednisone, prednisolone, cloprednol, deflazacort, fluocortin, triamcinolone, dexamethasone, methylprednisolone, fluprednisolone, clocortolone, clobetasone, alclomethasone, flumethasone, fluoprednidene, fluorandrenolone, betamethasone, beclomethasone, fluocortolone, mometasone, fluticasone, halomethasone, fluocinolone, diflorasone, desoximethasone, fluocinonide, amcinonide, halcinonide, diflucortolone, clobetasol and paramethasone. Examples for mineralcorticoids are aldosterone, deoxycorticosterone and fludrocortisone, and examples for androgens are dehydroepiandrosterone (DHEA) and estrogens. The corticosteroid may be used as a free compound or in the form of a salt, ester or prodrug. In preferred embodiments the corticosteroid used is triamcinolone, cortisone, hydrocortisone, prednisolone or prednisone.

In preferred embodiments the pharmaceutical compositions according to the invention and/or the kit according to the invention are intended for use in the treatment of joint diseases such as osteoarthritis, arthritis, joint inflammation and inflammatory loss of cartilage, tendon conditions, degenerative spinal diseases and also autoimmune diseases. The osteoarthritis to be treated may be caused by excess strain, have congenital or traumatic causes or be the result of another disease such as an inflammation. The osteoarthritis to be treated is preferably an activated osteoarthritis or an inflammatory osteoarthritis. The pharmaceutical compositions according to the invention may be used in the treatment of osteoarthritis and arthritis in any joint like for example knee joint, hip joint, ankle joint, shoulder joint, vertebral joints, finger joints, cubital joint, toe joints, temporomandibular joint and wrist joint. The arthritis to be treated may be an arthritis caused by an infection such as bacterial arthritis or an arthritis not caused by an infection such as rheumatoid arthritis, psoriatic arthritis or gouty arthritis. Alternatively the pharmaceutical composition according to the invention and/or the kit according to the invention may also be intended for the use in the treatment of a disease different from one or more of the mentioned diseases (e.g. rheumatoid arthritis). The degenerative spinal disease to be treated may be a herniated disc for example. Autoimmune diseases comprise inter alia autoimmune diseases of the joints like for example Morbus Bechterew, rheumatoid arthritis and systemic lupus erythematodes as well as other autoimmune diseases like particularly neurodermitis and alopecia areata.

The pharmaceutical compositions according to the invention and/or the kit according to the invention are preferably intended for local administration. Thus in preferred embodiments they are intended for injection, particularly injection into the body region to be treated, particularly into the affected joint, into the affected nerve root or into the affected disc or into the local environment thereof. The pharmaceutical composition is thus particularly intended for intraarticular and/or periradicular injection. Alternatively the pharmaceutical compositions according to the invention may be formulated for topical administration, particularly as a cream or gel or for systemic administration, particularly oral administration in the form of tablets, capsules or pastilles. The type of administration depends inter alia on the disease to be treated. In local osteoarthritis or degenerative spinal disease, local administration of the pharmaceutical compositions according to the invention is preferred. In preferred embodiments the pharmaceutical compositions according to the invention and/or the kit according to the invention are exclusively intended or suitable for an administration different from systemic administration.

The pharmaceutical compositions according to the invention are suitably formulated for the different types of administration in a manner known to the person skilled in the art. Thus a pharmaceutical composition suitable for injection preferably has the form of a solution or dispersion or also a dry form e.g. as a powder or lyophilisate, which must be dissolved in an appropriate solvent such as water before the injection. The pharmaceutical compositions according to the invention contain the cytokine antagonist and/or the corticosteroid in therapeutically effective amounts. The cytokine antagonist is thus present preferably in a concentration of 0.5 to 150 mg/dose in the pharmaceutical compositions containing the cytokine antagonist, but may also be present in a much lower concentration such as 1 ng/dose or more, for example between 1 and 1000 ng/dose. These lower dose concentrations may be used particularly in a combination with growth factors and/or in natural IL-1Ra preparations like for example compositions with Orthokine. The higher dose concentrations are preferred for example for recombinantly prepared cytokine antagonists like Anakinra. The corticosteroid preferably has a concentration of 1 to 80 mg/dose, more preferably 5 to 40 mg/dose in the pharmaceutical compositions containing the corticosteroid. Furthermore, the pharmaceutical compositions according to the invention may additionally contain one or more carriers and/or one or more excipients.

The pharmaceutical compositions of the invention may also be intended for a treatment of patients who had already undergone another treatment of the relevant disease, i.e. for example osteoarthritis, arthritis and/or degenerative spinal disease, particularly if this other treatment was not successful or the disease's symptoms at least partially returned after an initially successful treatment. In preferred embodiments this other treatment is a therapy with a cytokine antagonist like for example Anakinra or Orthokine but without a corticosteroid, or a therapy with a corticosteroid, especially a glucocorticoid as described above, but without a cytokine antagonist.

Patients in the sense of the invention may be humans or animals suffering from one of the diseases described herein.

Thus the pharmaceutical compositions according to the invention may be suitable for treatment of a human and/or an animal like for example a dog, a cat, a horse, a cow, a pig, a goat or a camel or similar.

In a further embodiment of the invention the pharmaceutical compositions according to the invention are intended for use in a combination therapy together with exosomes. Exosomes are small vesicles coated by a lipid membrane, which are found in the extracellular space for example of the human body. They are formed and secreted by cells by separation from the cellular plasma membrane. Normally these exosomes also contain proteins which they have adopted from their original cell.

The exosomes may be directly contained in the pharmaceutical composition according to the invention or are administered simultaneously or sequentially in a separate composition. The exosomes are preferably prepared from a blood sample, wherein the exosomes are preferably autologous or allogeneic in relation to the patient to be treated. Methods for the preparation and administration of exosomes are described for example in patent application WO 2006/007529 A2.

Consequently a preferred embodiment provides that the pharmaceutical compositions of the invention are intended for a treatment in which exosomes are first obtained from a patient's blood sample and then subsequently re-administered to this patient together with a cytokine antagonist and a corticosteroid.

In case the combination therapy involves exosomes obtained from a blood sample of a patient, it is preferred in some cases to carry out a centrifugation step with at least 100 000 g in order to concentrate the exosomes, as such high relative centrifugal forces are especially suitable for concentrating exosomes. This applies to the first, second, third, fourth, fifth and/or sixth aspect of the present invention (pharmaceutical composition comprising a corticosteroid together with a cytokine antagonist, pharmaceutical composition comprising a cytokine antagonist for use in a combination therapy together with a corticosteroid, pharmaceutical composition comprising a corticosteroid for use in a combination therapy together with a cytokine antagonist, kit and/or use of a cytokine antagonist/a corticosteroid). Preferably such a centrifugation step is carried out in the treatment of diseases where a high concentration of exosomes is reasonable, preferably in the treatment of rheumatoid arthritis. It is particularly preferred if such a centrifugation step is carried out generally in case the combination therapy involves exosomes obtained from a blood sample of a patient. The centrifugation step with at least 100 000 g is preferably carried out for at least 30 min, particularly at least 60 min, as increasing the concentration is especially effective.

DETAILED DESCRIPTION OF PREFERRED EMBODIMENTS

Examples

In the following, different case studies of patients with advanced osteoarthritis are described. These were treated with a combination therapy including a cytokine antagonist (e.g. recombinant IL-1Ra or IL-1Ra obtained from autologous blood samples) and a corticosteroid.

Abbreviations:
ri right
le left
ab ambilateral
IRO inner rotation
ORO outer rotation
VAS visual analogue scale for sensation of pain (0 to 10)
WOMAC Patient questionnaire regarding osteoarthritis
CRP c-reactive protein, an inflammation marker traceable in blood
CFJ coxofemoral joint 1. Local Administration of Anakinra and Cortisone Case I: A., 69 years
Diagnosis: Coxarthrosis ri, degree III-IV in the X-ray; hip pain with limping for approx. 3 years, patient does not want hip replacement; clinical protective limping, IRO/ORO ri hip 5/0/5, additional finding of borreliosis known;
Therapy: 5× weekly injections of 1 mg Anakinra with 10 mg triamcinolone were administered.
Result: At the end of the therapy (after the $5^{th}$ session) the protective limping was gone. IRO/ORO ri now 10/0/15; VAS improved from 8 to 3; 70% pain reduction (personal assessment by the patient according to current pain degree (here 30%) compared to the pain before the treatment (100%), the pain reduction is the difference between current pain and pain before treatment (100%-30%=70%)). After a 3-month check-up unchanged improvement compared to the status at the end of the therapy.
Case II: R., 54 years, female
Diagnosis: clinically and radiologically moderate rhizarthrosis ri with strong pain (VAS 6) with function impediment when gripping objects. Cortisone injections in the past without success.
Therapy: A five-times injection treatment for the right thumb saddle joint consisting of 0.5 mg Anakinra in combination with 1 mg triamcinolone (in the $1^{st}$, $3^{rd}$ and $5^{th}$ session) was carried out.
Result: Pain free at the end of the therapy, 100% improvement; VAS now 0; normal function of the right hand; 3 months after the end of the therapy a continuously unchanged very good result at the checkup.
Case III: 49 years, male
Diagnosis: Clinically and radiologically moderate knee osteoarthritis ab degree II-III for many years. Hyaluronic acid injections and cortisone injections into the knee unsuccessful in the past.
Therapy: A 6-times Anakinra treatment using 10 mg triamcinolone at the $1^{st}$, $3^{rd}$ and $5^{th}$ session was carried out.
Result: At the end of the therapy 100% improvement of pain ri knee, le knee 70% improvement of pain
Case IV: T., 45 years, male, musician
Diagnosis: Radiological and clinical impingement le shoulder for approx. 2 years; previous cortisone injections without success; abduction limited by about 15 degrees
Therapy: An injection of 50 mg Anakinra with 10 mg Triam as well as a checkup were carried out. The injection of Anakinra and 10 mg Triam was mixed in a syringe and drawn up sterilely.
Result: At the subsequent checkup one week after the treatment completely pain free (100%), normal function. Due to the success of the therapy no further treatments were planned. Subsequent checkups were without pathological findings.
Case V: K., 45 years, male
Diagnosis: Clinically and radiologically medial knee osteoarthritis ri degree IV and retropatellar for many years; externally it was advised to try transposition osteotomy or a knee replacement ri. Patient however desired trying a conservative therapy. In the past, injections of hyaluronic acid and cortisone (triamcinolone) were without clinical success.

Therapy: A 10-times Anakinra treatment (100 mg per session) with parallel administration of 10 mg triamcinolone (total treatment dose 50 mg) twice weekly was carried out.
Result: At the end of the therapy 65% pain reduction after 3 months.

Case VI: M., 50 years, male
Diagnosis: Clinical and radiological (MRT) inner meniscus injury ri knee III with clear function deterioration and pain medial right knee. Surgery was recommended, patient would like non-surgical alternative.
Therapy: A one-time injection of 10 mg triamcinolone and 1 mg Anakinra was administered.
Result: One month after injection 80% pain improvement, patient does not want surgery any more but another injection, as this was very helpful. At the checkup 6 months after the therapy still no surgery desired, patient pain free.

Case VII: G., 42 years, male
Diagnosis: Clinically and radiologically low facet arthrosis for many years, additional finding diverticulum. In-patient treatment with cortisone injections into the low facets without success.
Therapy: 6 therapy sessions twice weekly with injections of 6 mg Anakinra into the low facets were carried out. With the first injection 3 mg triamcinolone were additionally administered, in the following treatments 2-6 exclusively 6 mg Anakinra were administered.
Result: 60% pain improvement, VAS improved from 7 before treatment to 3 after treatment. Checkups unchanged after 5 months.

TABLE 1

Therapy with Anakinra and Cortisone.
Statistic Evaluation of a Case Series

| Pain level before | Pain level after |
|---|---|
| 100 | 30 |
| 100 | 0 |
| 100 | 30 |
| 100 | 0 |
| 100 | 35 |
| 100 | 0 |
| 100 | 40 |
| 100 | 60 |
| 100 | 40 |
| 100 | 50 |
| 100 | 80 |
| 100 | 50 |

Number of patients: N=12
Average pain reduction: 71.5% after approx. 3 months (before therapy 100% pain, end of therapy 28.5% pain)
Standard deviation: SD=22
P<0.001
Thera with Orthokine and cortisone in osteoarthritis:
Number of patients: N=129
Average checkup period of time: 3 months
Average pain reduction: 71% (i.e. reduction of 100% pain before treatment to 29% after treatment)
Remarkably rapid onset of effect 2. Local Administration of Anakinra and Cortisone and Exosomes Case VIII: T., 56 years, female
Diagnosis: Clinically radiologically there is medial and retropatellar gonarthrosis le, degree IV. Externally a total knee replacement le was already planned.
Therapy: 3 injections of exosomes combined with Anakinra and 10 mg triamcinolone into the left knee (twice weekly) in order to avoid knee surgery
Result: At the time of the $3^{rd}$ injection 100% pain improvement, clear functional improvement. Surgery was cancelled, patient was still pain free 5 months after the end of the therapy 3. Local Administration of Anakinra and Cortisone and Orthokine Case IX: L., 57 years, male
Diagnosis: Strong shoulder pain le for 6 months (VAS 8); since then markedly disturbed sleep. Patient could hardly sleep during the last 6 months, hence also disturbed sense of well-being. Numerous injections with cortisone into the left shoulder were without success. Surgery appointment for the left shoulder was made. Here it should be tried to avoid surgery. Radiological and clinical signs of a partial rotator cuff rupture and subacromial constriction with complete shoulder stiffness le; Unpleasant sensations left arm with weakness of strength of hand and forearm left, degree 4.
Therapy: The injections were administered dorsally and laterally into the left shoulder. 2 ml Orthokine were administered into the shoulder with 10 mg Anakinra and 10 mg triamcinolone via a syringe. The therapy was carried out on 4 consecutive days.
Result: Already on the $2^{nd}$ treatment day the patient indicated an extreme improvement of pain with a pain reduction of 90%. VAS fell from 8 to 1, the shoulder was free and normally moveable. The patient was able to sleep through the night for the first time in 6 months. The patient thus experienced a clear improvement in his well-being. The therapy was continued until day 4. There was still an unchanged clear improvement as on treatment day 2, the checkup 6 months after the treatment revealed an unchanged positive finding. Surgery was cancelled, mobility was free, the patient can lift suitcases and books above shoulder height again without problems.

Case X: F., 45 years, female
Diagnosis: Complete stiffness of the shoulder ri for approx. 8 months. All previous therapies were without success, surgery was planned. The patient wanted to try another conservative treatment. Sleep at night had not been possible for several weeks. Beginning shoulder pain on the left, main finding was however the right shoulder which had VAS 9 with severe acute attacks up to 10, thus in total reduced general health.
Therapy: Treatment of the right shoulder with a combination of 2 mi Orthokine administered separately together with another syringe with a combination of 150 mg Anakinra and 5 mg triamcinolone on 6 consecutive days.
Result: 85% pain improvement from the $5^{th}$ day. Sleeping through the night was possible since the $2^{nd}$ treatment, thus significantly improved general health. VAS at the end of the treatment at the first checkup 8 months after the treatment still showed a very good unchanged result; surgery was cancelled.

4. Exosomes Incubated with IL-1Ra and Triamcinolone/Prednisolone

Case XI: S., 25 years, male
Diagnosis: Severe juvenile rheumatoid arthritis since approx. 15 years. Treatment with 25 mg Enbrel 2× weekly, 10 mg methotrexate, 5 mg decortin and naproxen 2×1 per day. Massive synovitis and pain both CFJ and both shoulders.

Abduction 60 degrees of both shoulders before treatment. Laboratory CRP value: 5.35 (normal value up to 0.5 mg); leukocytosis.

Therapy: Blood was taken for preparing exosomes in a 6 ml syringe (Orthokine syringe). Then 24 h incubation at 37 degrees, wherein when filling the syringe with blood, 1 mg Anakinra (IL-1Ra) and 2 mg prednisolone were given into the syringe beforehand. After several steps of centrifugation (up to 100 000 g) the mixture was then administered into patient's CFJs and the shoulders.

Result: After 3 days beginning significantly reduced swelling of the joints. Clinical and chemical checkup after 9 days: 80% pain improvement, CFJ normal, no swelling. CRP value now 1.93. Improvement also in other affected joints which were not locally injected. General quality of life was significantly improved. At the checkup after 3 months the situation remains stable. VAS 9 before treatment, since the first week after injection VAS 3. Patient very satisfied, can continue his work.

---

What is claimed is:

1. A pharmaceutical composition comprising:
a corticosteroid together with a cytokine antagonist and a further cytokine antagonist, wherein the cytokine antagonist is a recombinant interleukin antagonist IL-1Ra protein and the further cytokine antagonist is a naturally occurring interleukin antagonist IL-1Ra protein, wherein the recombinant interleukin antagonist IL-1Ra protein is anakinra and the naturally occurring interleukin antagonist IL-1Ra protein is obtained from human blood, and wherein the pharmaceutical composition is suitable for local administration.

2. The pharmaceutical composition of claim 1, further comprising a growth factor.

3. The pharmaceutical composition according to claim 2, wherein the pharmaceutical composition is prepared for simultaneous or sequential administration of the cytokine antagonists, the growth factor and the corticosteroid.

4. The composition according to claim 2, wherein the growth factor is selected from the group consisting of TGF-β, IGF, BMP, HGF and VEGF.

5. The pharmaceutical composition according to claim 1, wherein the cytokine antagonist is present in a concentration of 0.5 to 150 mg/dose.

6. The pharmaceutical composition according to claim 1, wherein the corticosteroid is one or more selected from the group of:
(a) a glucocorticoid, or a salt, ester or prodrug thereof;
(b) a mineral corticoid, or a salt, ester or prodrug thereof; and
(c) an androgen, or a salt, ester or prodrug thereof.

7. The pharmaceutical composition of claim 6, wherein the glucocorticoid is one or more from the group consisting of, cortisone, hydrocortisone, prednisone, prednisolone, cloprednol, deflazacort, fluocortin, triamcinolone, dexamethasone, methylprednisolone, fluprednisolone, clocortolone, clobetasone, alclomethasone, flumethasone, fluoprednidene, fluorandrenolone, betamethasone, beclomethasone, fluocortolone, mometasone, fluticasone, halomethasone, fluocinolone, diflorasone, desoximethasone, fluocinonide, amcinonide, halcinonide, diflucortolone, clobetasol, parametasone;
wherein the mineral corticoid is selected from the group consisting of aldosterone, deoxycorticosterone, and fludrocortisone; and
wherein the androgen is dehydroepiandrosterone (DHEA) or estrogens.

8. The pharmaceutical composition according to claim 1, wherein the corticosteroid is present in a concentration of 1 to 80 mg/dose.

9. The pharmaceutical composition according to claim 1, wherein the local administration is selected from the group consisting of injection into an affected body region, and topical administration.

10. The pharmaceutical composition according to claim 1, wherein the pharmaceutical composition further contains a carrier and/or an excipient.

11. A kit, comprising a pharmaceutical composition comprising a cytokine antagonist, a pharmaceutical composition comprising a corticosteroid, and a further cytokine antagonist, wherein the cytokine antagonist is a recombinant interleukin antagonist IL-1Ra protein, and the further cytokine antagonist is a naturally occurring interleukin antagonist IL-1Ra protein, wherein the recombinant interleukin antagonist IL1Ra protein is anakinra and the naturally occurring interleukin antagonist IL-1Ra protein is obtained from human blood, and wherein the pharmaceutical compositions are suitable for local administration.

12. The kit of claim 11, wherein the naturally occurring antagonist IL-1Ra protein is autologous serum in which IL-1Ra was enriched and is contained therein among other factors (Orthokine®) and the recombinant interleukin antagonist IL-1Ra protein is anakinra.

13. The kit of claim 11, the pharmaceutical composition comprising the cytokine antagonists, further comprising a growth factor.

14. A method of preparing a pharmaceutical preparation comprising the following steps:
providing a corticosteroid, a cytokine antagonist and a further cytokine antagonist, wherein the cytokine antagonist is a recombinant interleukin antagonist IL-1Ra protein and the further cytokine antagonist is a naturally occurring interleukin antagonist IL-1Ra protein, wherein the recombinant interleukin antagonist IL-1Ra protein is anakinra, the naturally occurring interleukin antagonist IL-1Ra protein is obtained from human blood, and
admixing said corticosteroid, said cytokine antagonist and said further cytokine antagonist with a suitable carrier, wherein the pharmaceutical composition is suitable for local administration.

15. The method of claim 14, further comprising the step of adding a growth factor to the pharmaceutical composition.

16. A pharmaceutical composition comprising,
a corticosteroid together with a cytokine antagonist and a further cytokine antagonist, wherein the cytokine antagonist is a recombinant interleukin antagonist IL-1Ra protein, and the further cytokine antagonist is a naturally occurring interleukin antagonist IL-1Ra protein wherein the recombinant interleukin antagonist IL-1Ra protein is obtained from *E. coli* and the naturally occurring IL-1Ra is obtained from human blood, and wherein the pharmaceutical composition is suitable for local administration.

17. A pharmaceutical composition comprising,
a corticosteroid together with a cytokine antagonist and a further cytokine antagonist, wherein the cytokine antagonist is a recombinant interleukin antagonist IL-1Ra protein, and the further cytokine antagonist is a naturally occurring interleukin antagonist IL-1Ra protein, wherein the recombinant interleukin antagonist IL-1Ra protein is anakinra, and the naturally occurring interleukin antagonist IL-1Ra is Orthokine®, and wherein the pharmaceutical composition is suitable for local administration.

18. A kit, comprising: a pharmaceutical composition comprising a cytokine antagonist, a pharmaceutical composition comprising a corticosteroid, and a further cytokine antagonist, wherein the cytokine antagonist is a recombinant interleukin antagonist IL-1Ra protein, and the further cytokine antagonist is a naturally occurring interleukin antagonist IL-1Ra protein, wherein the recombinant interleukin antagonist IL-1Ra protein is obtained from *E. coli* and the naturally occurring interleukin antagonist IL-1Ra protein is obtained from human blood, and wherein the pharmaceutical compositions are suitable for local administration.

19. A kit comprising: a pharmaceutical composition comprising a cytokine antagonist, a pharmaceutical composition comprising a corticosteroid, and a further cytokine antagonist, wherein the cytokine antagonist is a recombinant interleukin antagonist IL-1Ra protein, and the further cytokine antagonist is a naturally occurring interleukin antagonist IL-1Ra protein, wherein the recombinant interleukin antagonist IL-1Ra protein is anakinra and the naturally occurring interleukin antagonist IL-1Ra protein is Orthokine®, and wherein the pharmaceutical compositions are suitable for local administration.

20. A method of preparing a pharmaceutical composition, comprising the following steps:
providing a corticosteroid, a cytokine antagonist and a further cytokine antagonist, wherein the cytokine antagonist is a recombinant interleukin antagonist IL-1Ra protein and the further cytokine antagonist is a naturally occurring interleukin antagonist IL-1Ra protein, wherein the recombinant interleukin antagonist IL-1Ra protein is obtained from *E. coli* and the naturally occurring interleukin antagonist IL-1Ra protein is obtained from human blood, and
admixing said corticosteroid, said cytokine antagonist and said further cytokine antagonist with a suitable carrier, wherein the pharmaceutical composition is suitable for local administration.

21. A method of preparing a pharmaceutical composition, comprising the following steps:
providing a corticosteroid, a cytokine antagonist and a further cytokine antagonist, wherein the cytokine antagonist is a recombinant interleukin antagonist IL-1Ra protein and the further cytokine antagonist is a naturally occurring interleukin antagonist IL-1Ra protein, wherein the recombinant interleukin antagonist IL-1Ra protein is anakinra and the naturally occurring interleukin antagonist IL-1Ra protein is Orthokine®, and
admixing said corticosteroid, said cytokine antagonist and said further cytokine antagonist with a suitable carrier, wherein the pharmaceutical composition is suitable for local administration.

* * * * *